United States Patent [19]

Shami

[11] Patent Number: 4,668,685

[45] Date of Patent: May 26, 1987

[54] SUBSTITUTED BENZOATE ESTER PRODRUG DERIVATIVES OF 3-HYDROXYMORPHINANS, WHICH ARE ANALGESICS OR NARCOTIC ANTAGONISTS

[75] Inventor: Elie G. Shami, Huntington, N.Y.

[73] Assignee: E.I. Du Pont de Nemours and Company, Wilmington, Del.

[21] Appl. No.: 733,464

[22] Filed: May 14, 1985

Related U.S. Application Data

[63] Continuation-in-part of Ser. No. 627,923, Jul. 5, 1984.

[51] Int. Cl.$^4$ ............... A61K 31/485; C07D 489/12; C07D 489/02; C07D 221/28
[52] U.S. Cl. ................. 514/279; 514/282; 514/289; 546/39; 546/44; 546/45; 546/46; 546/63; 546/74
[58] Field of Search ............ 546/44, 45, 46, 74, 546/63, 39; 514/279, 282, 281, 289

[56] References Cited

U.S. PATENT DOCUMENTS

| 3,254,088 | 5/1966 | Lewenstein | 546/45 |
| 3,332,950 | 7/1967 | Blumberg et al. | 546/45 |
| 3,393,197 | 7/1968 | Patcher et al. | 546/44 |
| 4,161,597 | 7/1979 | Olofson et al. | 546/15 |

FOREIGN PATENT DOCUMENTS

| 0224197 | 7/1910 | Fed. Rep. of Germany | 546/44 |
| 2323192 | 12/1973 | Fed. Rep. of Germany | |
| M3195 | 3/1965 | France | 546/44 |
| 2004420 | 11/1969 | France | |
| 2184065 | 12/1973 | France | |
| 0184163 | 10/1984 | Japan | 546/74 |
| 184182 | 10/1984 | Japan | 546/39 |
| 184183 | 10/1984 | Japan | 546/39 |
| 186987 | 10/1984 | Japan | 546/39 |
| 1097167 | 12/1967 | United Kingdom | |

OTHER PUBLICATIONS

Bartels-Keith, et al., J. Chem. Soc. (C), pp. 434-440 (1967).
Selmeci, et al., Chemical Abstracts, vol. 70, 88011h (1969).
Selmeci, et al., Chemical Abstracts, vol. 70, 4324b (1969).
Braun, et al., Berichte, vol. 49, pp. 2655-2663 (1916).
Beilstein, Series EII, vol. 27, pp. 154, 157 (1955).
Burce, et al., Chemical Abstracts, vol. 87, 73416w (1977).
Legostev, Chemical Abstracts, vol. 53, 10561e (1959).
Brunner, et al., Chemical Abstracts, vol. 86, 65340f (1977).
Shionogi, Co., Chemical Abstracts, vol. 68, 59448j (1968).
Shionogi Co., Chemical Abstracts, vol. 73, 4076j (1970).
Smith Kline & French Ltd., Chemical Abstracts, vol. 64, 1904b (1966).
Progress in Drug Research, vol. 8, 1965, pp. 261-320, Archer and Harris.
Venuti, *Synthesis*, 266-268 Apr. (1982).
Derwent Abstract 23,188, Abstract Eire Patent 627/66, 06/16/66.

Primary Examiner—Donald G. Daus
Assistant Examiner—Diana G. Rivers

[57] ABSTRACT

Substituted benzoate ester prodrug derivatives of 3-hydroxymorphinans are useful as analgesics or narcotic antagonists and provide enhanced bioavailability of 3-hydroxymorphinans from orally administered doses.

30 Claims, No Drawings

SUBSTITUTED BENZOATE ESTER PRODRUG DERIVATIVES OF 3-HYDROXYMORPHINANS, WHICH ARE ANALGESICS OR NARCOTIC ANTAGONISTS

RELATIONSHIP TO OTHER APPLICATIONS

This application is a continuation-in-part of copending application Ser. No. 627,923, filed July 5, 1984.

BACKGROUND OF THE INVENTION

1. Field of Invention

This invention relates to substituted benzoate ester prodrug derivatives of 3-hydroxymorphinans, pharmaceutical compositions comprising prodrugs of 3-hydroxymorphinans and a suitable pharmaceutical carrier, methods of treating pain or reversing the effects of narcotic drugs such as morphine in a mammal using the prodrug, methods for preparing the prodrug, nitrobenzoate intermediates useful in the preparation of the prodrug, and a method for preparing the intermediates. The prodrugs provide enhanced bioavailability of 3-hydroxymorphinans from orally administered doses.

2. Prior Art

U.S. Pat. No. 3,393,197 issued to Pachter and Matossian on July 16, 1968 disclose N-substituted-14-hydroxydihydronormorphines, including the N-cyclobutyl-methyl derivative, commonly called nalbuphine. These compounds combine the properties of being narcotic antagonists as well as analgesics.

Morphine, oxymorphone, hydromorphone, and levorphanol are well known strong narcotic analgesics which can unfortunately be addictive and/or euphoric and are subjected to abuse by parenteral administration.

Heretofore many compounds have been prepared which have the 3-hydroxymorphinan ring nucleus, including several derivatives having various substituents on the nitrogen atom thereof. It has also been found that these compounds not only have analgetic properties but some have narcotic antagonist properties.

U.S. Pat. No. 3,254,088 issued to Lewenstein on May 31, 1966 discloses N-allyl-7,8-dihydro-14-hydroxynormorphinone commonly known as naloxone. U.S. Pat. No. 3,332,950 issued to Pachter and Matossian on July 25, 1967, discloses N-substituted-14-hydroxydihydronormorphinones including the N-cyclopropylmethyl analog commonly known as naltrexone. Compounds of these two patents are narcotic antagonists.

The definition of narcotic antagonism adopted in the present invention is that of Archer and Harris, in their Chapter on this topic in Progress in Drug Research, Vol. 8, 1965, pages 261 to 320, wherein narcotic antagonists are defined as compounds which "have the remarkable property of reversing the major pharmacodynamic actions of the narcotics . . . . Strictly speaking we consider a substance to be a narcotic antagonist if it can reverse the more prominent effects of morphine such as analgesia, sedation, respiratory depression and myosis."

German Pat. No. 2,323,192 issued to Endo Labs, Inc. on Apr. 26, 1973 discloses long-acting injectable narcotic antagonist preparations consisting essentially of a compound of the formula

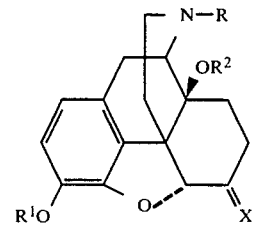

wherein:
R is allyl or cyclopropyl methyl,
$R^1$ includes benzoyl or substituted benzoyl,
$R^2$ is H or $R^1$, and
X is O or a ketal, and a vegetable oil suitable for subcutaneous or intramuscular administration. This patent further discloses that the duration of narcotic antagonist activity for the preparations in vegetable oil is prolonged as compared to the corresponding aqueous preparations. This patent also discloses the reaction of N-substituted-7,8-dihydro-14-hydroxynormorphinones with one equivalent of an acid chloride ($R^5$COCl) in the presence of a base, such as an alkali carbonate or bicarbonate, or in the presence of a tertiary amine, such as pyridine or triethylamine.

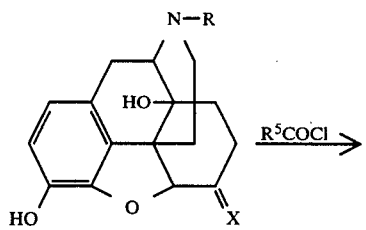

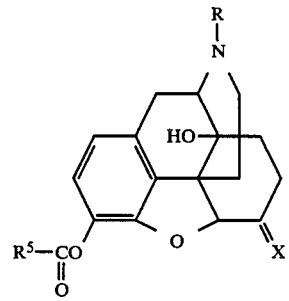

Venuti, Synthesis, 266 to 268 (1982), discloses the reaction of isatoic anhydride with a variety of simple amines and alcohols in the presence of 4-dimethylaminopyridine to prepare anthranilamides and anthranilate esters. Only monofunctional alcohols and amines are used, and the use of substituted isatoic anhydrides in the reaction is not disclosed.

The oral administration of many drugs will elicit a substantially lesser response as compared to an equal dosage administered parenterally. This reduction in potency most commonly results from the extensive metabolism of the drug during its transit from the gastrointestinal tract to the general circulation. For example, the liver and intestinal mucosa, through which an orally administered drug passes before it enters the circulatory system, are very active enzymatically and can thus metabolize the drug in many ways.

When an orally administered drug is metabolized rapidly by the gastrointestinal system or liver prior to entering the circulatory system, its bioavailability is low. In certain instances, this problem can be circumvented by administering the drug by another route. Examples of such alternative routes include nasal (propanalol), sublingual (nitroglycerin) or inhalation (cromolyn sodium). Drugs administered by these routes avoid hepatic and gut-wall metabolism on their way to the systemic circulation.

In some instances, the presystemic metabolism of certain orally administered drugs can be overcome by derivatization of the functional group in the molecule that is susceptible to gastrointestinal hepatic metabolism. This modification protects the group from metabolic attack during the absorption process or first pass through the liver. However, the masking group must ultimately be removed to enable the drug to exert its maximum effect. This conversion may take place in blood or tissue. These types of masked drugs are usually referred to as prodrugs.

A desired characteristic of a prodrug is that it is pharmacologically and toxicologically inert until cleaved into its two components. Also, it is important that the chemical group used to alter the parent drug be relatively non-toxic, since it will eventually be released in the body.

There are a number of examples in the literature which demonstrate the feasibility of the prodrug concept. However, it is apparent from these published studies that each drug class must be considered by itself. There is no way to accurately predict which prodrug structure will be suitable for a particular drug. A derivative which may work well for one drug may not do so for another. Differences in absorption, metabolism, distribution, and excretion among drugs do not permit generalizations to be made about prodrug design.

Many of the above 3-hydroxymorphinans are potent narcotic antagonist and/or analgesics which undergo extensive gastrointestinal and/or first pass metabolism upon oral delivery, and thus have decreased bioavailability. None of the references cited, nor any known references, suggest the novel substituted benzoate esters of 3-hydroxymorphinans of the instant invention, or their desirability as prodrugs of 3-hydroxymorphinans.

SUMMARY OF THE INVENTION

According to the present invention, provided are substituted benzoate esters of 3-hydroxymorphinans, particularly those of the formulas (I) and (II):

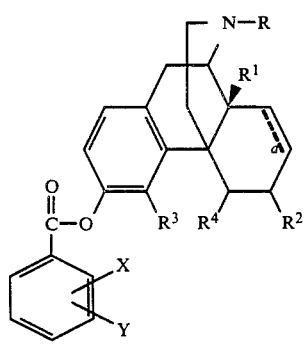

(I)

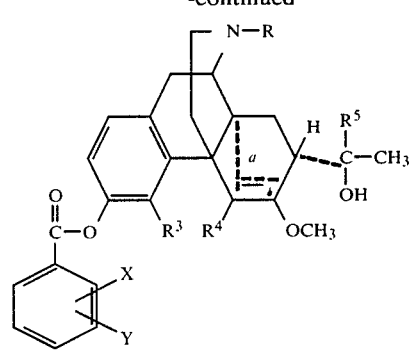

(II)

or their pharmaceutically acceptable acid addition salts, wherein:

a is a single bond, or double bond;

R is methyl, allyl, methylallyl, cyclopropylmethyl, or cyclobutylmethyl;

$R^1$ is hydrogen, or OH;

$R^2$ is hydrogen, OH, or =O;

$R^3$ and $R^4$ are hydrogen, or taken together are —O—;

$R^5$ is t-butyl or n-propyl;

X and Y are individually selected from H, $OR^6$, $NHR^6$ and $NR^6R^7$, provided that at least one of X or Y is $OR^6$, $NHR^6$, or $NR^6R^7$;

$R^6$ is H, $C_1$–$C_4$ alkyl, or $COR^8$;

$R^7$ is $C_1$–$C_4$ alkyl, or $COR^8$; and $R^8$ is H, or $C_1$–$C_4$ alkyl.

Also provided are analgesic or narcotic antagonist pharmaceutical compositions containing an effective analgesic amount or narcotic antagonist amount of a prodrug of Formula (I) or Formula (II) and a suitable pharmaceutical carrier.

Also provided are methods of treating pain or reversing the effects of a narcotic drug such as morphine in a mammal which comprise administering to the mammal an effective analgesic or narcotic antagonistic amount of a compound of Formula (I) or Formula (II).

In addition, further provided are processes for preparing the prodrugs of Formula (I) or Formula (II) which comprises contacting a 3-hydroxymorphinan with an acylating agent in the presence or absence of a base.

Additionally provided are processes for preparing the prodrugs of Formula (I) or Formula (II) wherein when X is $NH_2$ and Y is selected from H, $OR^6$ or $NR^6R^7$, wherein $R^6$ and $R^7$ are individually $C_1$–$C_4$ alkyl, or $COR^8$, the process comprises (a) contacting a 3-hydroxymorphinan with a nitrobenzoyl chloride or a nitrobenzoic acid in the presence of a catalyst to form a nitrobenzoate; and (b) hydrogenating or reducing the nitrobenzoate.

Nitrobenzoate intermediates of the prodrugs of Formula (I) and Formula (II) are provided wherein the intermediates are of the formulas:

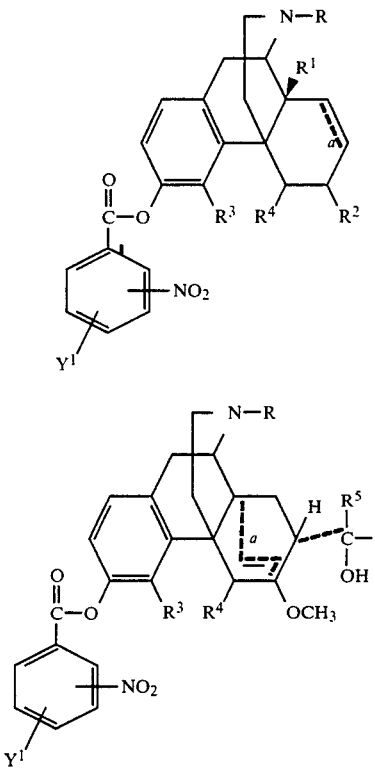

wherein
a is a single or double bond;
R-R[8] are as defined above; and
Y[1] is selected from H, OR[6] or NR[6]R[7].

Lastly provided are processes for preparing the prodrug intermediates of Formula (IA) or Formula (IIA) which comprises contacting 3-hydroxymorphinan with a nitrobenzoyl chloride or a nitrobenzoic acid in the presence of a catalyst.

DETAILED DESCRIPTION OF THE INVENTION

Preferred compounds of Formula (I) and Formula (II) include those wherein X at the 2-position is OR[6] or NHR[6], and Y at the 4-position is H or OR[6]; or a pharmaceutically acceptable acid addition salt thereof. These compounds are preferred because of the high percentage of the 3-hydroxymorphinan made bioavailable upon their oral administration.

Especially preferred are:
nalbuphine-3-anthranilate hydrochloride (X=2—NH₂.HCl, Y=H)
nalbuphine-3-(acetylsalicylate) (X=2—CH₃CO₂, Y=H)
nalbuphine-3-(N-methylanthranilate)hydrochloride (X=2—NHCH₃.HCl, Y=H)
nalbuphine-3-(2,4-dimethoxybenzoate) (X=2—CH₃O, Y=4—CH₃O)
nalbuphine-3-salicylate (X=2—OH, Y=H)
naltrexone-3-anthranilate (X=2—NH₂, Y=H)
naloxone-3-anthranilate (X=2—NH₂, Y=H)
butorphanol-3-anthranilate (X=2—NH₂, Y=H)
buprenorphine-3-anthranilate hydrochloride (X=2—NH₂.HCl, Y=H)
buprenorphine-3-(acetylsalicylate) (X=2—CH₃CO₂, Y=H)
buprenorphine-3-salicylate hydrochloride (X=2—OH, Y=H)

The following table shows important 3-hydroxymorphinans and their relationships to the structures of Formulas (I) and (II):

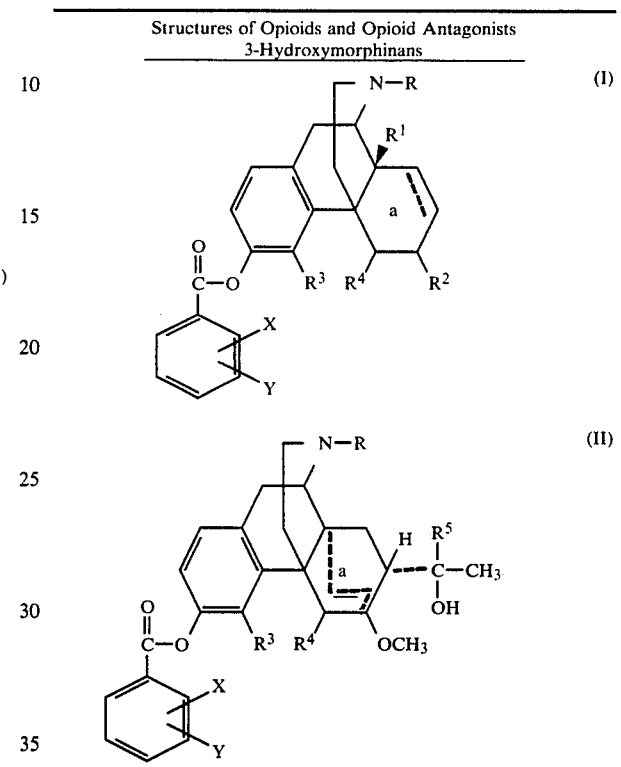

| | Structures of Opioids and Opioid Antagonists 3-Hydroxymorphinans | | | | | |
|---|---|---|---|---|---|---|
| | R | R[1] | a | R[2] | R[3] R[4] | R[5] |
| I | | | | | | |
| morphine[a] | CH₃ | H | double | H / \ OH | O | — |
| butorphanol[b] | CH₂—△ | OH | single | H₂ | H H | — |
| nalbuphine[b] | CH₂—△ | OH | single | H / \ OH | O | — |
| naloxone[c] | CH₂CH=CH₂ | OH | single | =O | O | — |
| naltrexone[c] | —CH₂—◁ | OH | single | =O | O | — |
| oxymorphone[a] | CH₃ | OH | single | =O | O | — |
| dihydromorphine | CH₃ | H | single | H / \ OH | O | — |
| hyrdomorphone[a] | CH₃ | H | single | =O | O | — |
| levorphanol[a] | CH₃ | H | single | H₂ | H H | — |
| II | | | | | | |
| buprenorphine[d] | CH₂—◁ | — | single | — | O | t-Bu |

Structures of Opioids and Opioid Antagonists
3-Hydroxymorphinans

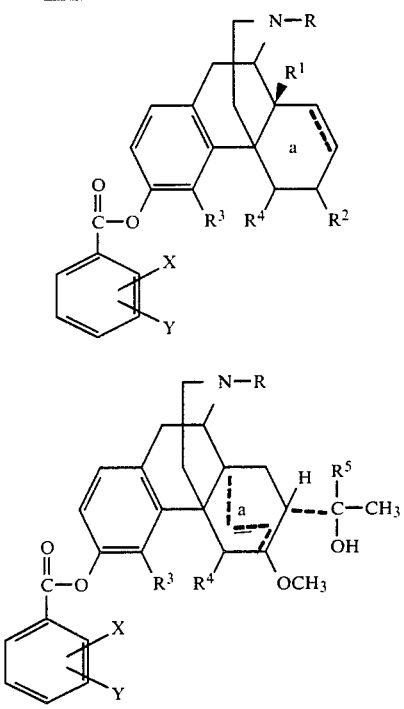

| | R | R¹ | a | R² | R³ | R⁴ | R⁵ |
|---|---|---|---|---|---|---|---|
| etorphine[a,e] | CH₃ | — | double | — | O | | n-Pr |

[a] opioid analgesic (opioid agonist)
[b] produces analgesia, mixed agonist/weak antagonist
[c] opioid antagonist (no analgesia)
[d] semisynthetic opioid derived from thebaine, 25–50× more potent than morphine (partial agonist)
[e] 1000× as potent as morphine By the term "alkyl" is meant straight or branched-chain alkyl.

By the term "pharmaceutically acceptable acid addition salt" is meant any non-toxic pharmaceutically suitable salt of a compound of Formula (I) or Formula (II) which has analgesic, narcotic antagonist, or antagonist-analgetic properties in mammals. Preparation of such salts is well known to those skilled in pharmaceuticals. Pharmaceutically acceptable acid addition salts of compounds of Formula (I) or Formula (II) include the hydrochloride, hydrobromide, hydroiodide, sulfate, bisulfate, nitrate, citrate, tartrate, bitartrate, lactate, phosphate, malate, maleate, fumarate, succinate, acetate and pamoate.

As used herein:

Nalbuphine means (−)-17-(Cyclobutylmethyl)-4,5α-epoxymorphinan-3,6α,14-triol or a salt thereof.

Naltrexone means (−)-17-(Cyclopropylmethyl)-4,5α-epoxy-3,14-dihydroxymorphinan-6-one or a salt thereof.

Naloxone means (−)-17-Allyl-4,5α-epoxy-3,14-dihydroxymorphinan-6-one or a salt thereof.

Butorphanol means (−)-17-(Cyclobutylmethyl)morphinan-3,14-diol or a salt thereof.

Oxymorphone means (−)-4,5α-Epoxy-3,14-dihydroxy-17-methylmorphinan-6-one or a salt thereof.

Morphine means (−)-7,8-Didehydro-4,5α-epoxy-17-methylmorphinan-3,6α-diol or a salt thereof.

Hydromorphone means (−)-4,5α-Epoxy-3-hydroxy-17-methylmorphinan-6-one or a salt thereof.

Levorphanol means (−)-17-Methylmorphinan-3-ol or a salt thereof.

Buprenorphine means (−)-17-(Cyclopropylmethyl)-α-(1,1-dimethylethyl)-4,5-epoxy-18,19-dihydro-3-hydroxy-6-methoxy-α-methyl-6,14-ethenomorphinan-7-methanol or a salt thereof.

Etorphine means (−)-4,5α-Epoxy-3-hydroxy-6-methoxy-α,17-dimethyl-α-propyl-6,14-ethenomorphinan-7α-methanol or a salt thereof.

Synthesis

The compounds of Formula (I) or Formula (II) of the present invention may be prepared by contacting a 3-hydroxymorphinan with an acylating agent in the presence of a catalyst.

The acylating agents and catalysts used as starting reactants to make the compounds of Formula (I) and Formula (II) are known.

The acylating agents used in the process to prepare the prodrugs of Formula (I) and Formula (II) include substituted benzoyl halides, substituted benzoic anhydrides, mixed anhydrides, isatoic anhydrides, and substituted benzoic acids.

Methods A, B, C and D described hereinafter are set forth with respect to the compounds of Formula (I). However, it will be clear to one skilled in the art that these methods can also be used to prepare compounds of Formula (II).

As used herein, the term "Method A" refers to the process for preparing a compound of Formula (I) wherein the acylating agent is a substituted benzoyl halide, a substituted benzoic anhydride, or a mixed anhydride.

As used herein, the term "Method B" refers to the process for preparing a compound of Formula (I) wherein the acylating agent is an isatoic anhydride.

As used herein, the term "Method C" refers to the process for preparing a compound of Formula (I) wherein the acylating agent is a substituted benzoic acid.

METHOD A

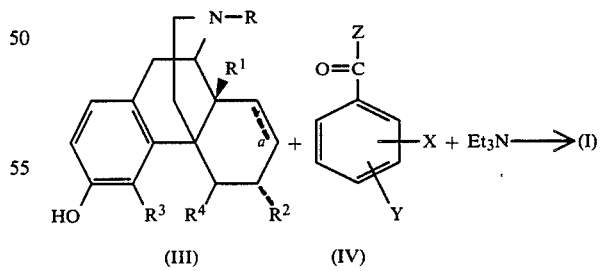

(IIIa) nalbuphine =

R is CH₂—⌬ ;

R¹ and R² are OH;
a is single;
R³ and R⁴ together are —O .

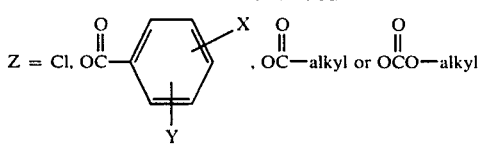

Method A provides compounds of Formula (I) wherein X and Y are individually selected from H, OR$^6$ or NR$^6$R$^7$, wherein R$^6$ and R$^7$ are individually C$_1$-C$_4$ alkyl or COR$^8$, provided that at least one of X or Y is OR$^6$ or NR$^6$R$^7$.

In Method A, a 3-hydroxymorphinan of Formula (III) is allowed to react with an acylating agent (IV), such as a substituted benzoyl chloride, benzoic anhydride or mixed anhydride, wherein X and Y are not OH or NHR$^6$, in an aprotic solvent, such as methylene chloride, tetrahydrofuran or 1,2-dimethoxyethane, in the presence of an organic base, such as triethylamine, N-methylmorpholine or pyridine, or an inorganic base, such as sodium carbonate. A solution of the activated benzoate in the reaction solvent is added to a solution of a 3-hydroxymorphinan in the reaction solvent containing the base at a temperature ranging from 0° C. to the boiling point of the solvent, generally from 0° C. to room temperature being preferred. The reactants are kept in contact from 0.5 to 24 hours, generally 5 to 20 hours.

METHOD B

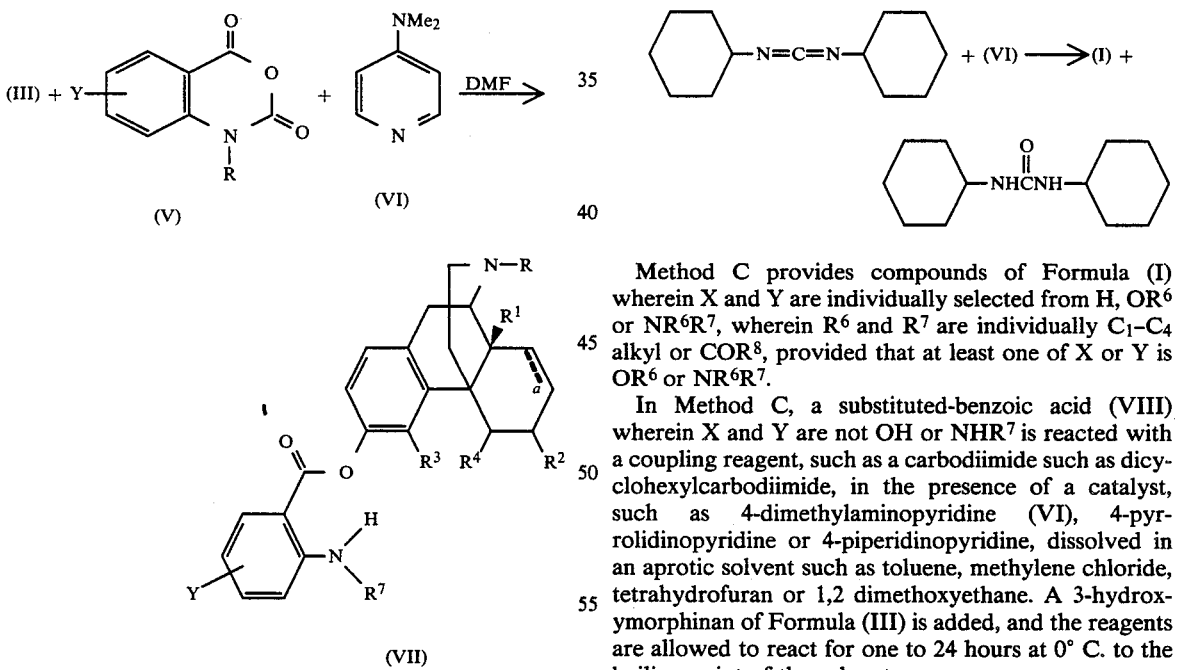

Method B provides compounds of Formula (I) wherein X is 2—NHR$^7$.

In Method B, a 3-hydroxymorphinan of Formula (III) is dissolved in a dipolar aprotic solvent, such as N,N-dimethylformamide (DMF), dimethylsulfoxide (DMSO), N-methylpyrrolidinone, N,N-dimethylacetamide (DMAC) or tripyrrolidinophosphine oxide. An isatoic anhydride (V) is added, followed by a catalyst, such as 4-dimethylaminopyridine (VI), 4-pyrrolidinopyridine or 4-piperidinopyridine. The solution is heated at 50° to 150° C. for one to five hours under nitrogen.

In Method B, compounds of Formula (VII) with various groups represented by R$^7$ are prepared from the corresponding substituted isatoic anhydrides, (V). Thus, reaction of N-methylisatoic anhydride with nalbuphine produces the compound of Example 12 in Table I (R$^7$=CH$_3$). Likewise reaction of N-acetylisatoic anhydride with nalbuphine yields the compound of Example 14 with Table I

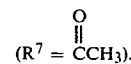

Also, reaction of N-formylisatoic anhydride with nalbuphine yields the compound of Example 19 in Table I

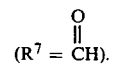

METHOD C

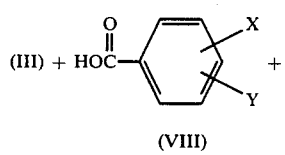

Method C provides compounds of Formula (I) wherein X and Y are individually selected from H, OR$^6$ or NR$^6$R$^7$, wherein R$^6$ and R$^7$ are individually C$_1$-C$_4$ alkyl or COR$^8$, provided that at least one of X or Y is OR$^6$ or NR$^6$R$^7$.

In Method C, a substituted-benzoic acid (VIII) wherein X and Y are not OH or NHR$^7$ is reacted with a coupling reagent, such as a carbodiimide such as dicyclohexylcarbodiimide, in the presence of a catalyst, such as 4-dimethylaminopyridine (VI), 4-pyrrolidinopyridine or 4-piperidinopyridine, dissolved in an aprotic solvent such as toluene, methylene chloride, tetrahydrofuran or 1,2 dimethoxyethane. A 3-hydroxymorphinan of Formula (III) is added, and the reagents are allowed to react for one to 24 hours at 0° C. to the boiling point of the solvent.

Compounds of Formula (I) may also be prepared by (a) contacting a 3-hydroxymorphinan with a nitrobenzoyl chloride or a nitrobenzoic acid in the presence of an acid scavenger to form a nitrobenzoate; and (b) hydrogenating or reducing the nitrobenzoate.

As used herein, the term "Method D" refers to the process for preparing a compound of Formula (I) wherein the nitrobenzoate formed from the reaction of a 3-hydroxymorphinan with a nitrobenzoyl chloride or a nitrobenzoic acid is hydrogenated.

METHOD D

Method D provides compounds of Formula (I) wherein X is NH₂ and Y is selected from H, OR⁶ or NR⁶R⁷, wherein R⁶ and R⁷ are individually C₁–C₄ alkyl or COR⁸.

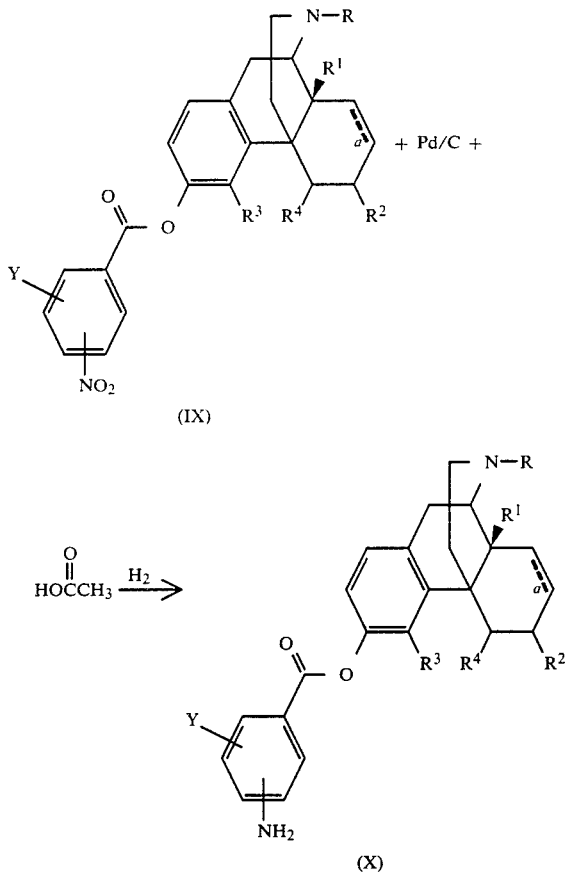

In Method D, the 3-hydroxymorphinan nitrobenzoates, except compounds where a is a double bond, may be hydrogenated to aminobenzoates (X) in a solvent such as methanol, ethanol or acetic acid, or in a mixture of an alcohol plus 5 to 10% acetic acid. The catalyst utilized may be 5 to 10% palladium on carbon or alumina, rhodium on carbon or alumina, or 5 to 10% platinum on carbon. Hydrogenation is conducted under hydrogen at atmospheric pressure to 60 psi at room temperature for one to six hours. If Raney nickel is used as the catalyst, a higher pressure, such as 100 to 1000 psi is utilized at a temperature from room temperature to 100° C. for five to 24 hours.

In compounds where a is a double bond, an alternate method of reduction (other than catalytic hydrogenation) must be employed so as not to reduce the double bond. The nitro group may be reduced with a metal such as iron or tin chloride in a protic solvent such as aqueous hydrochloric acid. Alternatively, reduction of the nitro group can be carried out with a mixture of sodium borohydride and a transition metal salt as catalyst, such as cobalt (II) chloride.

It will be clear to one skilled in the art that all Formula (X) compounds are included within the scope of the compounds of Formula (I).

Method A may be used to react 3-hydroxymorphinans (III) with a nitrobenzoyl chloride to prepare 3-hydroxymorphinan nitrobenzoates (IA). Also, Method C may be used to react a 3-hydroxymorphinan of Formula (III) with a nitrobenzoic acid to produce the nitrobenzoates. The nitrobenzoyl chloride and nitrobenzoic acid starting reagents used to produce the nitrobenzoates are known. The 3-hydroxymorphinan nitrobenzoates of Formula (IA) are useful as intermediates in the preparation of 3-hydroxymorphinan aminobenzoates of Formula (I).

EXAMPLE 1

METHOD A

Nalbuphine-3-(acetylsalicylate)

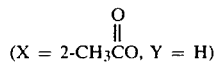

To a round bottom flask containing 35 mL methylene chloride was added and dissolved 3.57 g (0.01 mole) of nalbuphine. Then, 1.11 g (0.011 mole) triethylamine was added and the solution was cooled to 0° to 5° C. A solution of 2.18 g (0.011 mole) of acetylsalicyloyl chloride (III) in 25 mL methylene chloride was added dropwise with vigorous stirring under nitrogen at 0° to 5° C. After the addition was completed, the ice bath was removed and the reaction was stirred at ambient temperature for 5 hours. TLC (silica gel, 3:1 ethyl acetate-hexane) showed the desired product with a trace of nalbuphine remaining. The reaction mixture was washed once with 10% sodium carbonate and once with water, dried over sodium sulfate, filtered, and evaporated. The remaining solid was triturated with ether, filtered and air dried to yield 4.6 g nalbuphine 3-(acetylsalicylate), mp 165°–168° C. TLC showed the product at Rf 0.22 and impurities at Rf 0.01 and 0.09.

This material was purified by medium pressure LC using 15 to 25 micron silica gel in a column 50 mm in diameter and 300 mm long. The product was dissolved in methylene chloride and added onto the column. Elution with a 70:30 hexane-acetone mixture gave 3.6 g of pure product, mp 172°–173° C. TLC one spot, Rf 0.22. Analytical HPLC showed purity >99%.

EXAMPLE 2

METHOD B

Nalbuphine-3-anthranilate hydrochloride (X=2—NH₂.HCl, Y=H)

To a 50 mL round bottom flask was added 3.57 g (0.01 mole) of nalbuphine (Formula IIIa), 1.96 g (0.012 mole) of isatoic anhydride (V), 0.12 g (0.001 mole) of 4-dimethylaminopyridine and 25 mL DMF. The reaction mixture was then heated under nitrogen in an oil bath at 55° to 60° C. for 5 hours. The flask was removed from the oil bath and 25 mL water was added. The product precipitated out as dense crystals. After being at room temperature for 1 hour, the product was collected, washed with water and air dried. Yield 4.2 g; mp 199°–202° C. TLC (silica gel, 3:1 ethyl acetate-hexane) showed product at Rf 0.6 and an impurity at 0.16. The product was dissolved in methylene chloride and treated with charcoal to remove the tan color. Evaporation of the methylene chloride gave white crystals. One recrystallization from ethyl acetate gave 4.0 g of nalbuphine 3-anthranilate; mp 205°–206° C. TLC showed product at Rf 0.6. Analytical HPLC showed the product was 99% pure. The base was converted to the monohydrochloride by dissolving it in 10.0 mL tetrahydrofuran and adding 2.0 g of a 20% solution of HCl in ethanol dropwise. The monohydrochloride precipitated as white crystals. It was collected by filtration, washed with ether and air dried. Yield 4.1 g; mp 254° C.

EXAMPLE 3

Method C

Nalbuphine-3-(4-acetamidobenzoate)

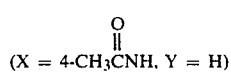

(X = 4-CH₃CNH, Y = H)

To 75 mL methylene chloride was added and dissolved 1.79 g (0.01 mole) of 4-acetamidobenozic acid (VIII), 2.27 g (0.011 mole) of dicyclohexylcarbodiimide and 0.2 g of 4-dimethylaminopyridine. Then, 3.57 g (0.01 mole) of nalbuphine was added and the reaction was stirred at room temperature for 24 hours. The precipitated dicyclohexylurea was filtered off and the filtrate was evaporated to yield an oil. This was dissolved in 10 mL of 1-propanol and allowed to crystallize. Recrystallization from ethyl acetate gave 3.5 g of nalbuphine-3-(4-acetamidobenzoate), mp 212°–214° C.

EXAMPLE 4

Method D

Nalbuphine-3-(4-aminobenzoate) (X=4-NH₂, Y=H)

Nalbuphine-3-(4-nitrobenzoate) was prepared following the procedure of Method A, mp 161°–162° C. from 1-propanol. Then, 6 g of nalbuphine-3-(4-nitrobenzoate) was dissolved in 200 mL ethanol, and 12 mL acetic acid was added. One-half g of 10% palladium on carbon was added, and the mixture was hydrogenated at 45 psi for 4 hours on a Parr Shaker. The catalyst was filtered off and the filtrate evaporated. The remaining oil was dissolved in 100 mL water, and made basic with ammonium hydroxide. The product precipitated and was collected by filtration, washed with water and dried. Yield 5.0 g; mp 212°–214° C. This was recrystallized from ethyl acetate (1 g/10 mL solvent) to give 3.8 g of nalbuphine-3-(4-aminobenzoate), mp 218°–219° C.

EXAMPLE 12

Method B

Nalbuphine-3-(N-methylanthranilate) (X=2-NHCH₃HCl, Y=H)

A solution of 7.14 g (0.02 mole) of nalbuphine, 5.38 g (0.03 mole) of N-methylisatoic anhydride, 600 mg (0.005 mole) of 4-dimethylaminopyridine in 35 mL DMF was heated in an oil bath at 55°–60° C. for 4 hours. Upon adding 35 mL water, a solid crystallized out, which was filtered off, washed with water and dried to yield 8.0 g. This was triturated with 30 mL ether, then recrystallized twice from 1-propanol to yield 3.65 g, mp 145°–146° C. The compound was converted to the monohydrochloride by dissolving it in THF and adding one equivalent of HCl gas in ether. The title compound which precipitated out was filtered off, washed with ether and dried. Yield 3.4 g; mp 202° C. (froth).

The compounds of Examples 1 to 4, and 12, other compounds which were prepared using the synthesis procedures described above, and compounds which can be prepared from nalbuphine by such procedures are shown in Table I.

TABLE I

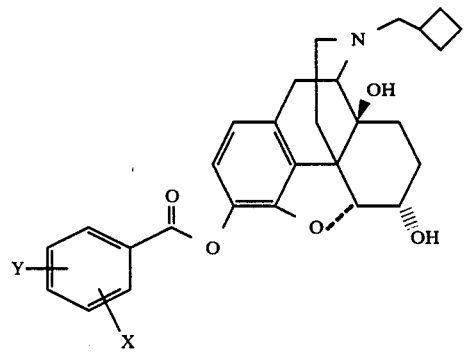

| Example No. | X | Y | Method of Preparation | Base/HCl Salt | m.p. (°C.) |
|---|---|---|---|---|---|
| 1 | 2-CH₃CO₂ | H | A | base | 172–3 |
| 2 | 2-NH₂ | H | B | HCl salt | 254 |
| 3 | 4-CH₃CONH | H | C | base | 212–4 |
| 4 | 4-NH₂ | H | D | base | 218–9 |
| 5 | 4-CH₃O | H | A | HCl salt | 234 (d) |
| 6 | 2-CH₃O | 5-CH₃O | A | HCl salt | 211 (d) |
| 7 | 3-CH₃O | 5-CH₃O | A | base | 140–2 |
| 8 | 3-NH₂ | H | D | di-HCl salt | 216–18 |
| 9 | 3-CH₃O | 4-CH₃O | A | base | 132–4 |
| 10 | 2-CH₃O | 4-CH₃O | A | base | 162–4 |
| 11 | 2-OH | H | C | base | 158–9 |
| 12 | 2-CH₃NH | H | B | HCl salt | 202 (d) |
| 13 | 4-(CH₃CH₂CH₂CH₂)₂N | H | C | | |
| 14 | 2-CH₃CONH | H | B | | |
| 15 | 2-CH₃CONH | 4-CH₃CONH | C | | |
| 16 | 3-CH₃CH₂O | H | A | | |
| 17 | 2-CH₃CO₂ | 6-CH₃CO₂ | C | | |

TABLE I-continued

| Example No. | X | Y | Method of Preparation | Base/HCl Salt | m.p. (°C.) |
|---|---|---|---|---|---|
| 18 | 2-CH$_3$(CH$_2$)$_2$CONH | 3-CH$_3$CH$_2$O | C | | |
| 19 | 2-HCONH | H | B | | |
| 20 | 2-OH | 6-NH$_2$ | C | | |
| 21 | 3-HCO$_2$ | 4-HCONH | C | | |
| 22 | 3-CH$_3$CO$_2$ | 5-CH$_3$(CH$_2$)$_3$O | C | | |

EXAMPLES 23 AND 24

Method B

Naloxone-3-anthranilate (Formula I where R=CH$_2$CH=CH$_2$; R$^1$=OH; a=single bond; R$^2$=O; R$^3$ and R$^4$=—O- - -; X=2-NH$_2$; Y=H)

Following the procedure of Method B described in Example 2, a mixture of 6.62 g (0.02 mole) of naloxone, 4.9 g (0.03 mole) of isatoic anhydride, 0.6 g (0.005 mole) of 4-dimethylaminopyridine in 20 mL of DMF was heated for 4 hours at 60° C. to afford 8.0 g of crude product, m.p. 199°–201° C. (base). Recrystallization first from ethyl acetate (6.9 g, m.p. 200°–201° C.) and then from methoxyethanol gave 5.4 g of naloxone-3-anthranilate; m.p. 206°–207° C. TLC (silica gel, ethyl acetate) showed the product as one spot at R$_f$=0.65. Conversion of the base to the monohydrochloride followed by recrystallization from ethanol gave 5.4 g (m.p. 233° C. frothing).

EXAMPLE 25

Method A

Naloxone-3-(acetylsalicylate) hydrochloride (Formula I where R=CH$_2$CH=CH$_2$; R$^1$=OH; a=single bond; R$^2$=O; R$^3$ and R$^4$=—O- - -; X=2-CH$_3$CO$_2$; Y=H)

Following the procedure of Method A described in Example 1, 10 millimoles of naloxone yielded 4.1 g of naloxone-3-(acetylsalicylate) hydrochloride, m.p. 262°–263° C.

EXAMPLE 26

Method B

Naltrexone-3-anthranilate (Formula I where

R = CH$_2$—◁ ;

R$^1$=OH; a=single bond; R$^2$=O; R$^3$ and R$^4$=—O- - -; X=2-NH$_2$; Y=H)

Following the procedure of Method B described in Example 2, 3.45 g (0.01 mole) of naltrexone, 1.63 g (0.01 mole) of isatoic anhydride, 0.25 g (0.002 mole) of 4-dimethylaminopyridine in 50 mL DMF gave 1.5 g of naltrexone-3-anthranilate, which was purified by recrystallization (twice) from 1-propanol, m.p. 181°–182° C.

EXAMPLE 27

Method A

Naltrexone-3-(acetylsalicylate) hydrochloride (Formula I where

R = CH$_2$—◁ ;

R$^1$=OH; a=single bond; R$^2$=O; R$^3$ and R$^4$=—O- - -; X=2-CH$_3$CO$_2$; Y=H)

Following the procedure of Method A described in Example 1, 10 millimoles of naltrexone yielded 3.9 g of naltrexone-3-acetylsalicylate hydrochloride, m.p. 247°–248° C.

EXAMPLE 28

Method B

Oxymorphone-3-anthranilate (Formula I where R=CH$_3$; R$^1$=OH; a=single bond; R$^2$=O; R$^3$ and R$^4$=—O- - -; X=2-NH$_2$; Y=H)

Following the procedure of Method B described in Example 2, a mixture of 10.0 g (0.033 mole) of oxymorphone, 7.01 g (0.043 mole) of isatoic anhydride, 1.2 g (0.01 mole) of 4-dimethylaminopyridine in 50 mL of DMF was heated for 5 hours at 60° C. The crude product (8.1 g) was recrystallized twice from ethyl acetate to give 7.05 g of oxymorphone-3-anthranilate, m.p. 225°–227° C.

EXAMPLE 29

Method B

Butorphanol-3-anthranilate (Formula I were

R = CH₂—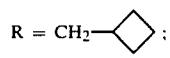;

R$^1$=OH; a=single bond; R$^2$=H; R$^3$ and R$^4$=H; X=2NH$_2$; Y=H)

Following the procedure of Method B described in Example 2, 1.3 g (3.97 mmole) of butorphanol, 0.71 g (4.37 mmole) of isatoic anhydride, 0.5 g (4.37 mmole) of 4-dimethylaminopyridine in 10 mL of DMF were heated for 5 hours at 55° C. The crude product (1.6 g, m.p. 167°–171° C.) was recrystallized from 5 mL of 1-propanol to yield 1.3 g of butorphanol-3-anthranilate, m.p. 177°–179° C. TLC (acetone/hexane 35:65) showed the product as a single spot at R$_f$=0.45.

The compounds of Examples 23–29 and other compounds which could be prepared using the synthesis procedures described above are shown in Table II.

TABLE II

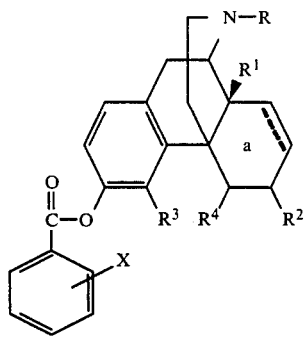

| Ex. No. | R | R$^1$ | a* | R$^2$ | R$^3$ | R$^4$ | X | Method of Preparation | HCl Salt | m.p. (°C.) |
|---|---|---|---|---|---|---|---|---|---|---|
| 23 | CH$_2$CH=CH$_2$ | OH | s | =O | O | | 2-NH$_2$ | B | base | 206–207 |
| 24 | CH$_2$CH=CH$_2$ | OH | s | =O | O | | 2-NH$_2$ | B | HCl salt | 233 |
| 25 | CH$_2$CH=CH$_2$ | OH | s | =O | O | | 2-CH$_3$CO$_2$ | A | HCl salt | 262–263 |
| 26 | CH$_2$—◁ | OH | s | =O | O | | 2-NH$_2$ | B | base | 181–182 |
| 27 | CH$_2$—◁ | OH | s | =O | O | | 2-CH$_3$CO$_2$ | A | HCl salt | 247–248 |
| 28 | CH$_3$ | OH | s | =O | O | | 2-NH$_2$ | B | base | 225–227 |
| 29 | CH$_2$—⬡ | OH | s | H$_2$ | H | H | 2-NH$_2$ | B | base | 177–179 |
| 30 | CH$_3$ | OH | s | =O | O | | 2-CH$_3$CO$_2$ | A | | |
| 31 | CH$_2$—⬡ | OH | s | H$_2$ | H | H | 2-CH$_3$CO$_2$ | A | | |
| 32 | CH$_3$ | H | d | OH | O | | 2-CH$_3$CO$_2$ | A | | |
| 33 | CH$_3$ | H | s | OH | O | | 2-NH$_2$ | B | | |
| 34 | CH$_3$ | H | s | =O | O | | 2-NH$_2$ | B | | |
| 35 | CH$_3$ | OH | s | =O | O | | 2-CH$_3$CO$_2$ | A | | |
| 36 | CH$_3$ | H | s | H$_2$ | H | H | 2-NH$_2$ | B | | |

*s = single bond
d = double bond

Compounds of Formula (II) which could be prepared using the synthesis procedures described above are shown in Table III.

TABLE III

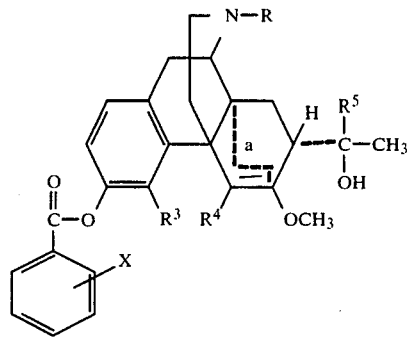

| Ex. No. | R | a | R$^3$ R$^4$ | R$^5$ | X | Method of Preparation |
|---|---|---|---|---|---|---|
| 37 | | single | O | t-butyl | 2-CH$_3$CO$_2$ | A |
| 38 | CH$_2$—◁ / CH$_2$—◁ | single | O | t-butyl | 2-NH$_2$ | B |
| 39 | CH$_3$ | double | O | n-propyl | 2-CH$_3$CO$_2$ | A |

TABLE III-continued

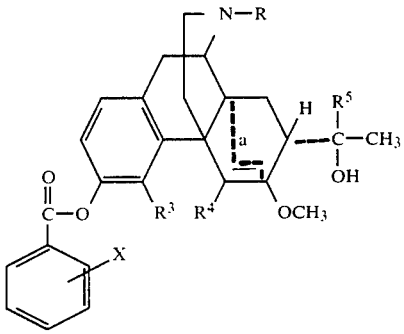

| Ex. No. | R | a | $R^3$ $R^4$ | $R^5$ | X | Method of Preparation |
|---|---|---|---|---|---|---|
| 40 | CH₃ | double | O | n-propyl | 2-NH₂ | B |

Dosage Forms

The prodrugs of the 3-hydroxymorphinans of Formula (I) and Formula (II) of the instant invention can be administered to treat pain by any means that produces contact of the active agent with the agent's site of action in the body of a mammal. They can be administered by any conventional means available for use in conjunction with pharmaceuticals, either as individual analgesic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of adminstration; age, health, and weight of the recipient; nature and extent of symptoms, kind of concurrent treatment, frequency of treatment, and the effect desired. Usually a daily dosage of prodrug can be about 0.1 to 50 milligrams per kilogram of body weight. Ordinarily, when the more potent compounds of this invention are used, 0.1 to 20, milligrams per kilogram per day, given in divided doses 2 to 4 times a day or in sustained release form, is effective to obtain desired results.

Dosage forms (compositions) suitable for internal administration contain from about 0.5 to 500 milligrams of prodrug per unit. In these pharmaceutical compositions the prodrug of Formula (I) or Formula (II) will ordinarily be present in an amount of about 0.5 to 95% by weight based on the total weight of the composition.

The prodrug of the instant invention can be administered orally in solid dosage forms, such as capsules, tablets, and powders, or in liquid dosage forms, such as elixirs, syrups, and suspensions.

Gelatin capsules contain the prodrug of Formula (I) or Formula (II) and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release prodducts to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

Suitable pharmaceutical carriers are described in Remington's Pharmaceutical Sciences, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered prodrug of Formula (I) or Formula (II), 150 milligrams of lactose, 24 milligrams of talc and 6 milligrams magnesium stearate.

Soft Gelatin Capsules

A mixture of a prodrug of Formula (I) or Formula (II) in soybean oil is prepared and injected by means of a positive displacement pump into gelatin to form soft gelatin capsules containing 75 milligrams of the prodrug. The capsules are washed in petroleum ether and dried.

Tablets

A large number of tablets are prepared by conventional procedures so that the dosage unit is 75 milligrams of the prodrug of Formula (I) or Formula (II), 0.2 milligrams of colloidal silicon dioxide, 5 milligrams of magnesium stearate, 250 milligrams of microcrystalline cellulose, 11 milligrams of cornstarch and 98.8 milligrams of lactose. Appropriate coatings may be applied to increase palatability or delay absorption.

Suppositories

The prodrug is added to a melted mixture of 80% polyethylene glycol 1000, 15% polyethylene glycol 4000, 0.15% methylparaben, 0.05% propylparaben and 4.8% water to a concentration of 75 milligrams per 3 grams. The molten mixture is poured into suppository molds and cast into suppositories weighing 3 grams each. They are frozen to solidify and packaged.

Suspension

An aqueous suspension is prepared for oral administration so that each 5 milliliters contain 75 milligrams of finely divided prodrug, 200 milligrams of sodium carboxymethyl cellulose, 5 milligrams of sodium benzoate, 1.0 grams of sorbitol solution, U.S.P., and 0.025 milliliters of vanillin.

Injectables

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques. Alternatively, when the prodrug is not stable in aqueous solution, the lyophillized prodrug may be dispensed in vials to be diluted with water prior to injection.

Utility

Test results indicate that the novel compounds of Formula (I) of this invention are useful in providing enhanced bioavailability of 3-hydroxymorphinans from orally administered dosages.

Methods

Among the experiments used to evaluate the 3-hydroxymorphinan prodrugs of the instant invention were measurements of their hydrolysis rates in rat and human plasma; and 3-hydroxymorphinan bioavailability in rats and dogs administered oral doses of the prodrug. 3-Hydroxymorphinan concentration was determined using high pressure liquid chromatography analytical procedures which measure 3-hydroxymorphinans concentration by electrochemical detection. This detector responds to the phenolic hydroxyl group (3-position) and thus does not detect prodrugs derivatized at this position. Plasma concentrations were determined after solvent extraction.

Plasma Hydrolysis

Prodrug was added to fresh plasmas (less than 24 hours after withdrawal) to a concentration of 0.28 μM, incubated at 37° C., and the rate of drug appearance was measured.

Oral 3-Hydroxymorphinan Bioavailability

Rats and dogs were administered the 3-hydroxymorphinans intravenously and orally, and the prodrugs of Formula (I) were administered orally. Usually, doses were administered as aqueous solutions prepared immediately before dosing, but some dogs received the drug or prodrug in solid form. Plasma was collected and frozen until analysis of 3-hydroxymorphinan concentration. The area under the plasma 3-hydroxymorphinan concentration versus time curve (AUC) was calculated for each animal. 3-Hydroxymorphinan bioavailability (F) was estimated by:

$$F = \frac{AUC^{po} \times Dose^{iv}}{AUC^{iv} \times Dose^{po}} \times 100\%$$

F represents the percentage of the administered dose absorbed into plasma. Relative bioavailability (RB) was determined by comparing the 3-hydroxymorphinan bioavailability from orally administered prodrug ($F_{pro}$) with the bioavailability of orally administered drug ($F_{drug}$).

$$RB = (F_{pro}/F_{drug})$$

Nalbuphine Results

With respect to both nalbuphine oral bioavailability and rates of in vitro prodrug hydrolysis in plasma, the dog was more similar to man than the rat and monkey were.

Table IV shows the percent bioavailability of oral nalbuphine in a variety of species. In terms of oral bioavailability of nalbuphine, the dog (5.4%) most closely resembles the human (14%) of those species examined.

TABLE IV

ORAL NALBUPHINE BIOAVAILABILITY
(% DOSE. MEAN ± SE)

| | |
|---|---|
| Rat | 2.7 ± 0.4[a] |
| Dog | 5.4 ± 0.9[b] |
| Monkey | 0.9, 1.6[b] |

TABLE IV-continued

ORAL NALBUPHINE BIOAVAILABILITY
(% DOSE. MEAN ± SE)

| | |
|---|---|
| Human | 14[c] |

[a]20 mg Nalbuphine /kg
[b]4 mg Nalbuphine /kg
[c]45 mg tablet or solution

Table V shows the hydrolysis half-life of two nalbuphine prodrugs in plasma from a variety of species. For both nalbuphine-acetylsalicylate (Example 1) and nalbuphine-anthranilate (Example 2) the half-life in plasma from dogs most closely approximates the half-life in human plasma.

TABLE V

NALBUPHINE PRODRUG HYDROLYSIS HALF-LIFE IN PLASMA t ½ (Hours)

| | NALBUPHINE-ACETYLSALICYLATE (Example 1) | NALBUPHINE-ANTHRANILATE (Example 2) |
|---|---|---|
| Rat | 0.2 | 1.5 |
| Dog | 2.8 | 14.6 |
| Monkey | 0.6 | 3.3 |
| Human | 6.2 | 45.0 |

Based on the results shown in Tables IV and V, the most important preclinical criterion in evaluating prodrugs is the oral bioavailability in dogs.

The relative bioavailability in dogs (RB) for a number of the prodrugs of 3-hydroxymorphinans of the instant invention is shown in Table VI.

TABLE VI

RELATIVE BIOAVAILABILITY OF 3-HYDROXYMORPHINAN DERIVATIVES WHEN ADMINISTERED AS PRODRUGS

| Example | RB in dogs (oral 3-hydroxymorphinan = 1) |
|---|---|
| 1 | 3.9 |
| 2 | 9.5 |
| 4 | 2.7 |
| 7 | 1.9 |
| 8 | 1.7 |
| 10 | 7.6 |
| 11 | 5.9 |
| 26 | 70.34 (±30.1) |

Percent bioavailability for Example 24 was 54.2 (±6.3)%. After oral naloxone HCl (10 mg naloxone/kg) plasma naloxone concentrations were close to the assay detection limits and as such were erratic, so relative bioavailability could not be calculated.

"Consisting essentially of" in the present disclosure is intended to have its customary meaning; namely, that all specified material and conditions are very important in practicing the invention but that unspecified materials and conditions are not excluded so long as they do not prevent the benefits of the invention from being realized.

What is claimed is:

1. A morphinan ester having the formula:

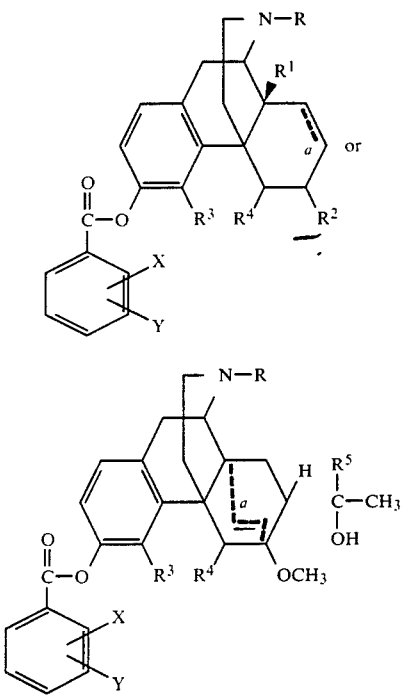

or a pharmaceutically acceptable acid addition salt thereof, wherein:
 a is a single bond, or double bond;
 R is methyl, allyl, methylallyl, cyclopropylmethyl, or cyclobutylmethyl;
 $R^1$ is H, or OH;
 $R^2$ is H, OH, or =O;
 $R^3$ and $R^4$ are H, or taken together are —O- - -;
 $R^5$ is t-butyl, or n-propyl;
 X at the 2-position is $OR^6$, $NHR^6$, or $NR^6R^7$;
 Y at the 4-position is H or $OR^6$;
 $R^6$ is H, $C_1$-$C_4$ alkyl, or $COR^8$;
 $R^7$ is $C_1$-$C_4$ alkyl, or $COR^8$; and
 $R^8$ is H, or $C_1$-$C_4$ alkyl.

2. A morphinan ester of claim 1 wherein the morphinan is selected from the group consisting of nalbuphine, naltrexone, naloxone, butorphanol, oxymorphone, morphine, hydromorphone, levorphanol, buprenorphine, and etorphine.

3. The compound of claim 1 which is nalbuphine-3-(acetylsalicylate).

4. The compound of claim 1 which is nalbuphine-3-anthranilate hydrochloride.

5. The compound of claim 1 which is nalbuphine-3-(2,4-dimethoxybenzoate).

6. The compound of claim 1 which is nalbuphine-3-salicylate.

7. The compound of claim 1 which is nalbuphine-3-(N-methylanthranilate) hydrochloride.

8. The compound of claim 1 which is naltrexone-3-anthranilate.

9. The compound of claim 1 which is naloxone-3-anthranilate.

10. The compound of claim 1 which is butorphanol-3-anthranilate.

11. A pharmaceutical composition consisting essentially of a suitable pharmaceutical carrier for oral administration and an effective analgesic amount or narcotic antagonist amount of a compound of claim 1.

12. A pharmaceutical composition consisting essentially of a suitable pharmaceutical carrier for oral administration and an effective analgesic amount or narcotic antagonist amount of a compound of claim 2.

13. A pharmaceutical composition consisting essentially of a suitable pharmaceutical carrier for oral administration and an effective analgesic amount of the compound of claim 3.

14. A pharmaceutical composition consisting essentially of a suitable pharmaceutical carrier for oral administration and an effective analgesic amount of the compound of claim 4.

15. A pharmaceutical composition consisting essentially or a suitable pharmaceutical carrier for oral administration and an effecctive analgesic amount of the compound of claim 5.

16. A pharmaceutical composition consisting essentially of a suitable pharmaceutical carrier for oral administration and an effective analgesic amount of the compound of claim 6.

17. A pharmaceutical composition consisting essentially of a suitable pharmaceutical carrier for oral administration and an effective analgesic amount of the compound of claim 7.

18. A pharmaceutical composition consisting essentially of a suitable pharmaceutical carrier for oral administration and an effective narcotic antagonist amount of the compound of claim 8.

19. A pharmaceutical composition consisting essentially of a suitable pharmaceutical carrier for oral administration and an effective narcotic antagonist amount of the compound of claim 9.

20. A pharmaceutical composition consisting essentially of a suitable pharmaceutical carrier for oral administration and an effective analgesic amount of the compound of claim 10.

21. A method of treating pain or reversing the effects of a narcotic drug in a mammal which comprises administering orally to the mammal an effective analgesic amount or narcotic antagonist amount of a compound of claim 1.

22. A method of treating pain or reversing the effects of a narcotic drug in a mammal which comprises administering orally to the mammal an effective analgesic amount or narcotic antagonist amount of a compound of claim 2.

23. A method of treating pain in a mammal which comprises administering orally to the mammal an effective analgesic amount of the compound of claim 3.

24. A method of treating pain in a mammal which comprises administering orally to the mammal an effective analgesic amount of the compound of claim 4.

25. A method of treating pain in a mammal which comprises administering orally to the mammal an effective analgesic amount of the compound of claim 5.

26. A method of treating pain in a mammal which comprises administering orally to the mammal an effective analgesic amount of the compound of claim 6.

27. A method of treating pain in a mammal which comprises administering orally to the mammal an effective analgesic amount of the compound of claim 10.

28. A method of reversing the effects of a narcotic drug in a mammal which comprises administering orally to the mammal an effective narcotic antagonist amount of the compound of claim 8.

29. A method of reversing the effects of a narcotic drug in a mammal which comprises administering orally to the mammal an effective narcotic antagonist amount of the compound of claim 9.

30. A method of treating pain in a mammal which comprises administering orally to the mammal an effective analgesic amount of the compound of claim 7.

* * * * *